United States Patent [19]
Nudenberg et al.

[11] Patent Number: 5,786,504
[45] Date of Patent: Jul. 28, 1998

[54] POLYMERIZATION CATALYST PROMOTER

[75] Inventors: Walter Nudenberg, Newton; Catherine Ann McGeary, Meriden; Xu Wu Feng, Bethany; Francis Xavier O'Shea, Naugatuck, all of Conn.

[73] Assignee: Uniroyal Chemical Company, Inc., Middlebury, Conn.

[21] Appl. No.: 649,736

[22] Filed: May 15, 1996

[51] Int. Cl.$^6$ .................. C07C 69/62; C07C 327/00
[52] U.S. Cl. ............................... 560/219; 558/250
[58] Field of Search ..................... 560/219; 558/250

[56] References Cited

U.S. PATENT DOCUMENTS 5,527,951  6/1996  Khan ............................ 560/219

FOREIGN PATENT DOCUMENTS 1215073  12/1986  Canada.
0134079   3/1985  European Pat. Off..
0151187  10/1981  German Dem. Rep..

OTHER PUBLICATIONS

CA 96: 151411 Oct. 8, 1981.
CA 100: 116493 Oct. 17, 1983.
CA 90: 71915 Sep. 21, 1978.

*Primary Examiner*—Paul J. Killos
*Attorney, Agent, or Firm*—Daniel Reitenbach

[57] ABSTRACT

Compounds of the formula:

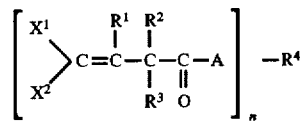

wherein
n is 1, 2, 3, or 4;
$X^1$ and $X^2$ are each, independently, chlorine or bromine;
A is O or S;
$R^1$ is hydrogen or $C_1$–$C_{16}$ alkyl;
$R^2$ is $C_1$–$C_{16}$ alkyl, $C_6$–$C_{16}$ aryl, $C_1$–$C_4$ alkylidene, or $CH_2OR^5$;
$R^3$ is hydrogen, chlorine, bromine, or $OR^6$;
$R^4$ is $C_1$–$C_{16}$ alkyl, $C_7$–$C_{16}$ aralkyl, $C_2$–$C_{16}$ alkenyl, or $C_6$–$C_{18}$ aryl;
$R^5$ is hydrogen, $C_1$–$C_{16}$ alkyl, $C_7$–$C_{16}$ aralkyl, $C_2$–$C_{16}$ alkenyl, or $C_6$–$C_{18}$ aryl; and
$R^6$ is hydrogen or $C_1$–$C_{16}$ alkyl.

These compounds by themselves and in combination with certain halo-but-2-enoic acids and esters are useful as catalyst promoters in ethylene polymerization processes.

23 Claims, No Drawings

POLYMERIZATION CATALYST PROMOTER

FIELD OF THE INVENTION

This invention relates to novel derivatives of halo-but-3-enoic acids and esters useful as catalyst promoters in ethylene polymerization. This invention also relates to a process for the preparation of alpha-olefin polymers in which ethylene, at least one higher alpha-olefin monomer and, optionally, a non-conjugated diene, are polymerized together to form an alpha-olefin copolymer, utilizing the novel derivatives of halo-but-3-enoic acids and esters.

BACKGROUND OF THE INVENTION

Polymerization of alpha-olefins to produce alpha-olefin copolymers is well established in the art. In these polymerizations a transition metal catalyst, most often a vanadium catalyst, and an organo-aluminum cocatalyst are added to a reaction mixture to catalyze the polymerization reaction. In order to enhance catalyst efficiency and/or regulate polymer molecular weight, a catalyst activator or promoter can also be employed.

U.S. application Ser. No. 08/372,689, filed on Jan. 12, 1995, now U.S. Pat. No. 5,527,951, describes a process for the polymerization of ethylene wherein the process is conducted in the presence of, inter alia, a catalyst promoter compound of the formula

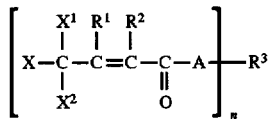

or a catalyst promoter compound of the formula

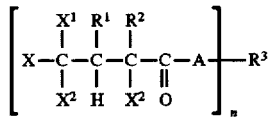

wherein, inter alia, n is 1, 2, 3, or 4; X, $X^1$, and $X^2$ are halogen; $R^1$ is hydrogen, halogen or alkyl; $R^2$ is hydrogen, halogen, alkyl, alkoxycarbonyl; A is O or S; and $R^3$ is hydrogen, alkyl, alkenyl or aryl.

European Patent 0 134 079 describes a process for preparing polyalpha-olefins wherein the process is conducted in the presence of, inter alia, a catalyst activator of the formula

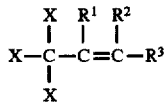

wherein X is chlorine or bromine, $R^1$ and $R^2$ are hydrogen, bromine or chlorine, and $R^3$ is a $C_2-C_{19}$ alkoxycarbonyl group.

It is the purpose of this invention to provide novel derivatives of halo-but-3-enoic acids and esters. It is a further purpose of this invention to provide novel catalyst promoters useful in a process for the preparation of alpha-olefin polymers.

SUMMARY OF THE INVENTION

This invention relates to a compound of the formula:

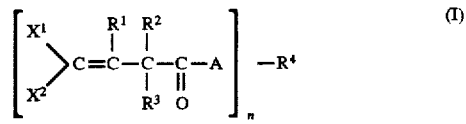

wherein n is 1, 2, 3, or 4;

$X^1$ and $X^2$ are each, independently, chlorine or bromine;

A is O or S;

$R^1$ is hydrogen or $C_1-C_{16}$ alkyl;

$R^2$ is $C_1-C_{16}$ alkyl, $C_6-C_{16}$ aryl, $C_1-C_4$ alkylidene, or $CH_2OR^5$;

$R^3$ is hydrogen, chlorine, bromine, or $OR^6$;

$R^4$ is $C_1-C_{16}$ alkyl, $C_7-C_{16}$ aralkyl, $C_2-C_{16}$ alkenyl, or $C_6-C_{18}$ aryl;

$R^5$ is hydrogen, $C_1-C_{16}$ alkyl, $C_7-C_{16}$ aralkyl, $C_2-C_{16}$ alkenyl, or $C_6-C_{18}$ aryl; and $R^6$ is hydrogen or $C_1-C_{16}$ alkyl, wherein $R^3$ is absent when $R^2$ is $C_1-C_4$ alkylidene.

DESCRIPTION OF THE INVENTION

Preferably, this invention relates to a compound of the formula

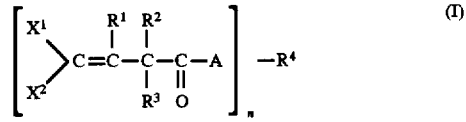

wherein n is 1 or 2, more preferably, 1;

$X^1$ and $X^2$ are each, independently, chlorine or bromine, more preferably, chlorine;

A is O or S, more preferably, O;

$R^1$ is hydrogen or $C_1-C_6$ alkyl, more preferably, hydrogen or $C_1-C_4$ alkyl;

$R^2$ is $C_1-C_6$ alkyl, $C_1-C_4$ alkylidene, or $CH_2OR^5$, more preferably, $C_1-C_4$ alkyl, $C_1-C_2$ alkylidene, or $CH_2OH$;

$R^3$ is hydrogen, chlorine, bromine, or $OR^6$, more preferably, hydrogen or chlorine;

$R^4$ is $C_1-C_6$ alkyl, $C_2-C_6$ alkenyl, or $C_6-C_{12}$ aryl, more preferably, $C_2-C_4$ alkyl, $C_2-C_4$ alkenyl, phenyl or naphthyl;

$R^5$ is hydrogen, $C_1-C_6$ alkyl, $C_2-C_6$ alkenyl, phenyl or naphthyl; and $R^6$ is hydrogen or $C_1-C_6$ alkyl, wherein $R^3$ is absent when $R^2$ is an alkylidene.

Particularly preferred are those compounds wherein n is 1;

$X^1$ and $X^2$ are each chlorine;

A is O;

$R^1$ is hydrogen or methyl;

$R^2$ is methyl, methylene, or $CH_2OH$;

$R^3$ is hydrogen or chlorine;

$R^4$ is $C_2-C_4$ alkyl, wherein $R^3$ is absent when $R^2$ is methylene.

The following compounds are illustrative of the compounds of this invention:

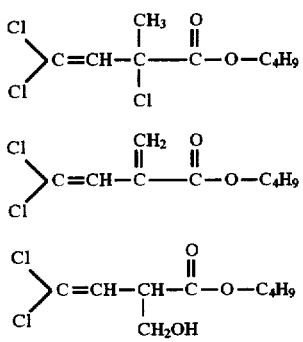

(1)

(2)

(3)

In general, the compounds of this invention can be prepared by heating a compound of the formula:

$$\left[\begin{array}{ccc} X^1 & R^1 & R^2 \\ | & | & | \\ X^2-C-C=C-C-A \\ | & \phantom{=} & || \\ R^3 & & O \end{array}\right]_n \!\!-\!\!R^4 \quad (P)$$

wherein n, A, $X^1$, $X^2$, $R^1$, $R^2$, $R^3$, and $R^4$ are as described above,
at a temperature above about 130° C., to produce a compound of formula I.

Alternatively, the compounds of this invention can be prepared by heating a compound of the formula:

$$\left[\begin{array}{ccc} X^1 & R^1 & R^2 \\ | & | & | \\ X^2-C-C=C-C-A \\ | & \phantom{=} & || \\ R^3 & & O \end{array}\right]_n \!\!-\!\!R^4 \quad (P)$$

wherein n, A, $X^1$, $X^2$, $R^1$, $R^2$, $R^3$, and $R^4$ are as described above,
in the presence of an acid, to produce the compound of formula I.

Compound P can be prepared as described in U.S. application Ser. No. 08/372,689, filed on Jan. 12, 1995, now U.S. Pat. No. 5,527,951, or in Canadian Patent No. 1,215,073.

The present invention is also directed to a process for the polymerization of alpha-olefins. Specifically, the process of this invention is directed to the polymerization of ethylene, at least one monomer having the structural formula $CH_2$=CHQ where Q is an alkyl having 1 to 8 carbon atoms, and, optionally, a non-conjugated diene. Among the monomers (compounds having the formula $CH_2$=CHQ) preferred for use in the process of this invention are propylene, butene-1, pentene-1, hexene-1, 3-methylpentene-1, heptene-1, and octene-1. Preferred non-conjugated dienes are 5-ethylidene-2-norbornene, dicyclopentadiene, and 1,4-hexadiene. In a preferred embodiment, an alpha-olefin having a structural formula given above wherein Q is an alkyl of 1–3 carbon atoms is employed to produce a terpolymer. In a more preferred embodiment, the reactants are ethylene, propylene, and as the non-conjugated diene, 5-ethylidene-2-norbornene or dicyclopentadiene. The resultant product of this polymerization process is an ethylene-propylene-nonconjugated diene terpolymer (EPDM).

The polymerization reaction of this invention is characterized by being catalyzed by a catalyst composition comprising (a) a vanadium-containing compound; (b) an organo-aluminum compound; and (c) a catalyst promoter. Among the vanadium compounds that can be employed as the catalyst of the present invention are vanadium oxytrichloride, vanadium tetrachloride, vanadium acetyl acetonate, vanadyl bis-diethylphosphate, chloro neopentyl vanadate, and the vanadium-containing catalysts described in U.S. application Ser. No. 08/372,689, filed on Jan. 12, 1995, now U.S. Pat. No. 5,527,951.

In addition to the vanadium catalyst, the process of the present invention utilizes an organo-aluminum compound as a cocatalyst. Preferably, the organo-aluminum compound is an alkyl aluminum or an alkyl aluminum halide. Of the halide compounds, the chlorides are most preferred. Among the alkyl aluminum chlorides preferred for use in this invention are ethyl aluminum sesquichloride, ethyl aluminum dichloride, diethyl aluminum chloride and diisobutyl aluminum chloride. Ethyl aluminum sesquichloride and diethyl aluminum chloride are most preferred.

A further additive used in the process of the present invention is a catalyst promoter. A compound of formula I can be used alone or in combination with other compounds of formula I, as a catalyst promoter in the polymerization process of this invention.

The catalyst promoter can also be a composition comprising about 10–95 weight percent, preferably, 30–90 weight percent, of one or more of the compounds of formula I wherein n is 1, and about 5 to 90 weight percent, preferably, 10 to 70 weight percent, of one or more compounds selected from the compounds of the formula:

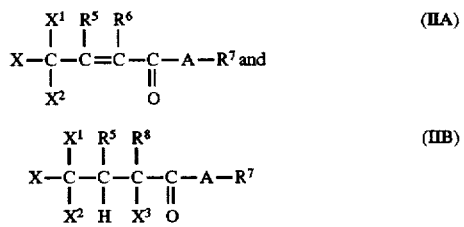

wherein:

X, $X^1$, $X^2$ and $X^3$ are each, independently, chlorine or bromine;

A is oxygen or sulfur;

$R^5$ is hydrogen or $C_1$–$C_{16}$ alkyl, preferably, hydrogen or $C_1$–$C_6$ alkyl;

$R^6$ is $C_1$–$C_{16}$ alkyl, preferably, $C_1$–$C_6$ alkyl;

$R^7$ is hydrogen, $C_1$–$C_{16}$ alkyl, $C_2$–$C_{16}$ alkenyl, or $C_6$–$C_{18}$ aryl, preferably, hydrogen or $C_2$–$C_{12}$ alkyl; and $R^8$ is hydrogen, $C_1$–$C_{16}$ alkyl or $C_1$–$C_4$ alkylidene, preferably, hydrogen or $C_1$–$C_6$ alkyl, wherein $X^3$ is absent when $R^8$ is $C_1$–$C_4$ alkylidene.

Compounds of formulas IIA and IIB can be prepared as described in U.S. application Ser. No. 08/372,689, filed on Jan. 12, 1995, now U.S. Pat. No. 5,527,951, or in Canadian Patent No. 1,215,073.

As a more preferred example, a composition useful as a catalyst promoter in the polymerization process of this invention can comprise about 30 to 90 weight percent of one or more of the following compounds of formula I:

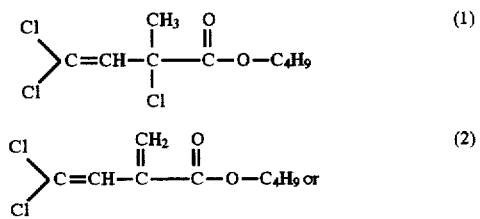

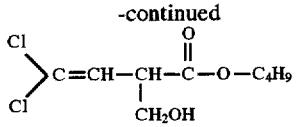

(3)

and about 10 to 70 weight percent of one or more compounds selected from the group consisting of

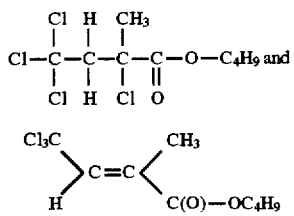

The polymerization process of this invention can typically be conducted in the following manner. The vanadium-containing compound (catalyst), the organoaluminum compound (cocatalyst), the catalyst promoter, reaction medium, and comonomers are introduced into a reaction vessel. The molar ratio of the catalyst promoter to the vanadium in the vanadium-containing compound is, preferably, in the range of between 3:1 and 80:1, more preferably, between 6:1 and 64:1, and most preferably, between 12:1 and 48:1.

The molar ratio of the cocatalyst to catalyst plus catalyst promoter is preferably in the range of between about 0.5:1 and about 500:1, more preferably, between about 1.5:1 and 100:1, and, most preferably, between about 2.5:1 and 10:1. The catalyst concentration can typically range between about $1 \times 10^{-8}$ and $3 \times 10^{-1}$ mole of vanadium per liter of total reaction medium.

The reaction medium is an inert medium such as, e.g., pentane, hexane, heptane, octane, isooctane, decane, benzene, toluene, and the like, optionally, in combination with liquid alpha-olefins.

The polymerization reaction is typically conducted in the liquid state at a temperature in the range of between about $-25°$ C. and about $70°$ C., for a time which can vary from several minutes or less to several hours or more depending on the specific reaction conditions and materials, typically, between about 15 minutes and 3 hours.

The following examples are provided to illustrate the present invention.

EXAMPLES

Example 1
Preparation of Butyl-2-methyl-2,4,4-trichlorobut-3-enoate

Butyl-2-methyl-4,4,4-trichloro-2-enoate (180 g., 0.7 mole, 87% assay by GC) was distilled at a pressure of 85 mm Hg with a pot temperature of 180°–200° C. and a vapor temperature of 156°–172° C., to produce 95.5 grams of a pale yellow distillate which was shown by GC/Mass Spectrometry (MS) and NMR to contain approximately 43% butyl-2-methyl-2,4,4-trichlorobut-3-enoate (A), and approximately 2% butyl-2-methylene-4,4-dichlorobut-3-enoate (B), and 45% residual butyl-2-methyl-4,4,4-trichloro-2-enoate starting material. Scaleup at high pot temperature (140° C.) and relatively high distillation pressures (30 mm Hg) produced a distillate containing 85–95% assay of A, with the pot residue composed primarily of dimers of B.

Example 2
Preparation of Butyl-2-methyl-2,4,4-trichloro-3-enoate and Butyl-2-hydroxymethyl-4,4-dichlorobut-enoate A reaction mixture of butyl-2-methyl-4,4,4-trichlorobut-2-enoate (65.9 grams, 0.25 mole), 20% aqueous hydrochloric acid (78.6 grams), and tetrabutyl ammonium bromide (4 grams, 0.0124 mole, 5 mole %) was heated at 105°–110° C. for 6.5 hours to produce 68% butyl-2-methyl-2,4,4-trichlorobut-3-enoate (A), 8% butyl-2-hydroxymethyl-4,4-dichlorobut-3-enoate (C), and 10% residual butyl-2-methyl-4,4,4-trichlorobut-2-enoate starting material. When the reaction mixture was heated for 37.5 hours, the product contained 60% A and 30% C. The reaction mixture was then cooled and extracted with 3×50 ml portions of diethyl ether, dried over MgSO₄, and distilled under vacuum to yield a distillate containing 53% A and 32% C. The identity of C was confirmed by GC/MS.

Example 3
Preparation of Butyl-2-methyl-2,4,4-trichloro-3-enoate and Butyl-2-hydroxymethyl-4,4-dichlorobut-enoate A 60/40 mixture of butyl-2-methyl-4,4,4-trichlorobut-2-enoate and butyl-2-methyl-2,4,4-trichlorobut-3-enoate (A) (258 grams, 1 mole) prepared by the thermal isomerization procedure described in Example 1, was stirred vigorously with 20% aqueous hydrochloric acid (300 grams) and tetrabutyl ammonium bromide (9 grams, 0.028 mole, 2.8 mole %) at 105°–110° C. for 13.5 hours to produce a crude reaction product containing 75% butyl-2-methyl-2,4,4-trichlorobut-enoate (A), 9% butyl-2-hydroxymethyl-4,4-dichlorobut-3-enoate (C), and 5% residual butyl-2-methyl-4,4,4-trichlorobut-2-enoate. Removal of the moisture followed by distillation at 73° C./0.1 mm Hg, yielded a distillate containing 83% A, 9% C, and 4% residual butyl-2-methyl-4,4,4-trichlorobut-2-enoate.

Example 4
Preparation of Butyl-2-methyl-2,4,4-trichloro-3-enoate and Butyl-2-hydroxymethyl-4 ,4-dichlorobut-enoate A 60/40 mixture of butyl-2-methyl-4,4,4-trichlorobut-2-enoate and butyl-2-methyl-2,4,4-trichlorobut-3-enoate (A) (50 grams, 0.2 mole) prepared by the thermal isomerization procedure described in Example 1, was stirred vigorously with 20% aqueous hydrochloric acid (125 grams) and tetrabutyl ammonium bromide (2 grams, 3 mole %), at 105°–110° C. for 22 hours to produce a crude reaction product containing 69% butyl-2-methyl-2,4,4-trichlorobut-enoate (A), 11% butyl-2-hydroxymethyl-4,4-dichlorobut-3-enoate (C), 3% residual butyl-2-methyl-4,4,4-trichlorobut-2-enoate, and approximately 8% high boiling material. The water was distilled from the crude reaction product at 65° C./0.1 mm Hg to produce a distillate containing 85% A, 11% C, and 2% residual butyl-2-methyl-4,4,4-trichlorobut-3-enoate.

Example 5 and Comparative Example A
Preoaration of EPDM in Solution Utilizing Butyl-2-methyl-2,4,4-trichloro-3-enoate and Comparative Activator Butyl-2-methyl-2 4 ,4,4-tetrachlorobutanoate A one gallon glass reactor equipped with temperature regulating coils was maintained at 30° C. and charged with 1.5 L of dry hexane and 4.2 mmole of ethylaluminum sesquichloride in 1.7 ml of hexane, and agitation was initiated. A 500 ml cylinder was pressurized with 1.5 psig of hydrogen, and the hydrogen was then charged into the reactor along with sufficient propylene to achieve a total pressure of 15 psig in the reactor. Ethylidene norbornene (ENB, 6 ml) was then added to the reactor. The reactor was then pressurized to 50 psig with a 1.5/1 weight ratio of ethylene and propylene. This gaseous ethylene/propylene mixture was fed continuously as required to maintain 50 psig pressure in the reactor throughout the polymerization. Vanadium oxytrichloride (VOCl$_3$, 0.075 mmole in 1.5 ml of hexane) and either butyl-2-methyl-2,4,4-trichloro-3-enoate or Comparative Activator butyl-2-methyl-2,4,4,4-tetrachlorobutanoate (1.5 mmole in 1.5 ml hexane), were then added to the reactor, followed 5 minutes later by an additional aliquot (4 ml) of the ENB. The temperature of the resultant reaction mixture in the reactor briefly rose to approximately 45° C. early in the polymerization process, but was cooled and maintained at 30° C. thereafter. After 0.5 hour, the reaction was terminated by addition of isopropyl alcohol and the resultant polymer product was washed, separated from the reaction mixture and analyzed. Results of such analysis for the polymer product prepared using butyl-2-methyl-2,4,4-trichloro-3-enoate and for the polymer product prepared using Comparative Activator butyl-2-methyl-2,4,4,4-tetrachlorobutanoate, are presented below in Table 1.

Catalyst Efficiency is presented in terms of pounds of polymer/pound of VOCl$_3$. The propylene composition and the Mooney Viscosity (ML 1+4 @ 125° C.) of the polymer products were determined using ASTM D-3900-86, Method D and ASTM D-1646-87, respectively. The ENB composition of the products was determined as described in I. J. Gardner and G. Ver Strate, Rubber Chemistry and Technology 46(4), 1019 (1973).

Compared to Comparative Activator butyl-2-methyl-2,4,4,4-tetrachlorobutanoate, the butyl-2-methyl-2,4,4-trichloro-3-enoate provided superior catalyst efficiency, superior propylene conversion, and molecular weight regulation (as shown by the Mooney viscosity).

TABLE 1

| Example | Calatyst Promoter[4] | Catalyst Efficiency[1] | % Propylene | % ENB | ML 1 + 4 @ 100° C. |
|---|---|---|---|---|---|
| A | Butyl-2-methyl-2,4,4,4-tetrachlorobutanoate[2] | 8154 | 25 | 8.2 | 83 |
| 1 | Butyl-2-methyl-2,4,4-trichlorobut-3-enoate[3] | 10077 | 31 | 6.9 | 48 |

[1]Pounds of polymer/pound of VOCl$_3$
[2]Determined by GC to be >98% butyl-2-methyl-2,4,4,4-tetrachlorobutanoate
[3]Prepared as described in Example 1 above. Determined by GC to be 93% butyl-2-methyl-2,4,4-trichlorobut-3-enoate, 1% butyl-2-methylene-4,4-dichlorobut-3-enoate, 2% butyl-2-methyl-4,4,4-trichlorobut-2-enoate, and 3% butyl-2-methyl-2,4,4,4-tetrachlorobutanoate.
[4]Mole ratio Promoter/vanadium = 20/1

In Examples 6, 7, 8, and 9, the catalyst promoter mpositions presented in Table 2 below were used.

TABLE 2

| Promoter Composition | Butyl-2-methyl-2,4,4-trichloro-but-3-enoate | Butyl-2-methyl-4,4,4-trichloro-but-2-enoate | Butyl-2-4,4,4-tetrachlorobutanoate |
|---|---|---|---|
| I | 12%[1] | 82% | 5% |
| II | 43% | 44% | 10% |
| III | 94% | 2% | 2% |

[1]Percentages determined by GC

Example 6
Preparation of Ethylene-Pro pylene Copolymer (EPM) in Suspension

Into a 3 liter stainless steel stirred autoclave (Buchi, Model BEP 280) with jacketed cooling, a dip tube for feeding ethylene, a thermocouple well, pressure gauge and ports for the introduction of hydrogen, propylene, and the catalyst components, was charged 780 grams of liquid propylene. The temperature was set at 15° C. by cooling the jacket with water from a circulating water bath. Ethylene was then added in an amount sufficient to raise the reactor pressure by 20 psig. A solution of 9.25 mmole of diethyl aluminum chloride in 16 ml of hexane from a pressurized bomb was then added to the Buchi followed by enough hydrogen gas to raise the pressure to 280 psig. 11 ml of a hexane solution containing 0.08 mmole of vanadium oxytrichloride and 1.28 mmole of Promoter Composition II (from Table 2) from a pressurized bomb was then charged to the Buchi all at once. The ensuing exotherm was controlled by the jacket cooling to maintain the temperature of 15° C. The pressure was maintained at 280 psig. by feeding ethylene into the Buchi to replace the ethylene which was being polymerized. Uptake of ethylene began to slow noticeably after 15 minutes and addition of ethylene was stopped after 36 minutes.

The contents of the Buchi were then transferred in increments to a two liter stainless steel pressure vessel (Parr reactor) containing 400 ml of hexane, 0.2 grams of octadecyl 3-(3',5'-di-tert-butyl-4'-hydroxyphenyl)-propionate as antioxidant and 10 ml of isopropanol to deactivate the catalyst. After each incremental transfer, propylene was vented from the Parr reactor to lower the pressure and the Buchi reactor was repressurized with nitrogen. Transfer was continued in this manner until all the contents of the Buchi were discharged and all the propylene had been vented off. The solution remaining in the Parr reactor was then removed and filtered through Celite. The hexane was then removed by distillation leaving a low molecular weight ethylene-propylene copolymer. Characteristics of this copolymer are presented in Table 3 below.

Example 7
Preparation of EPM in Suspension

The same procedure as described in Example 6 above was conducted except that Promoter Composition I was used instead of Promoter Composition II. The characteristics of the copolymer produced are presented in Table 3 below.

Example 8
Preparation of EPM in Solution

Into the Buchi autoclave described in Example 6, was charged 346 grams of hexane, 518 grams of propylene, 10 psig ethylene, 15.4 mmole of diethyl aluminum chloride, and 20 psig hydrogen. The temperature was maintained at 38° C. A hexane solution containing 0.01 mole/liter vanadium oxytrichloride and 0.046 mole/liter of Promoter Composition III was prepared to produce a catalyst/activator solution, and 20 ml of this catalyst/activator solution was pumped rapidly into the reactor. Exotherm began and was controlled by the jacket cooling to maintain the temperature at 38° C. Ethylene was then fed at 2 grams/minute and the catalyst/activator solution was pumped into the reactor at a rate sufficient to maintain a constant pressure. After 30 minutes, pumping of the catalyst/activator solution and feeding of the ethylene were terminated.

A solution of 0.15 grams of epoxidized soybean oil and 0.15 grams of octadecyl 3-(3',5'-di-tert-butyl-4'-hydroxyphenyl)propionate in 10 ml hexane was added and the propylene was slowly vented from the reactor. Another 400 grams of hexane was added to the reactor and the contents were heated to 49° C. The contents were then transferred to a 3 quart flint glass Chemco reactor containing 350 ml of deoxygenated distilled water. The mixture was agitated rapidly for 30 seconds and then allowed to settle for 20 minutes. A 600 ml portion of the washed hexane solution was then transferred to a second Chemco reactor and washed a second time with 160 ml of the deoxygenated distilled water. The twice washed hexane solution was then isolated and the hexane was removed by distillation to leave a low molecular weight ethylene-propylene copolymer. Characteristics of this copolymer are presented below in Table 3.

Example 9
Preparation of EPM in Solution

The same procedure as described above in Example 8 was conducted except that Promoter Composition I was used instead of Promoter Composition III. The characteristics of the copolymer produced are presented in Table 3 below.

TABLE 3

| Example | Promoter Composition | Efficiency[1] | Mv[2] | % Propylene[3] |
|---|---|---|---|---|
| 6 | II[4] | 13753 | 4300 | 52 |
| 7 | I[4] | 10260 | 4295 | 50 |
| 8 | III[5] | 2016 | 7512 | 59 |
| 9 | I[5] | 1517 | 7632 | 56 |

[1]Grams polymer/gram $VOCl_3$
[2]Number average molecular weight
[3]Weight percent in copolymer; determined using ASTM D-3900-86, Method D
[4]Mole ratio Promoter Composition/vanadium = 16/1
[5]Mole ratio Promoter Composition/vanadium = 4.6/1

What is claimed is:

1. A compound of the formula:

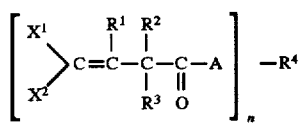

wherein n is 1, 2, 3, or 4;
$X^1$ and $X^2$ are each, independently, chlorine or bromine;
A is O or S;
$R^1$ is hydrogen or $C_1$–$C_{16}$ alkyl;
$R^2$ is $C_1$–$C_{16}$ alkyl, $C_6$–$C^{16}$ aryl, $C_1$–$C_4$ alkylidene, or $CH_2OR^5$;
$R^3$ is hydrogen, chlorine, bromine, or $OR^6$;
$R^4$ is $C_4$–$C_{16}$ alkyl, $C_2$–$C_{16}$ alkenyl, or $C_6$–$C_{18}$ aryl;
$R^5$ is hydrogen, $C_1$–$C_{16}$ alkyl, $C_7$–$C_{16}$ aralkyl, $C_2$–$C_{16}$ alkenyl, or $C_6$–$C_{18}$ aryl; and
$R^6$ is hydrogen or $C_1$–$C_{16}$ alkyl, wherein $R^3$ is absent when $R^2$ is $C_1$–$C_4$ alkylidene.

2. A compound as recited in claim 1 wherein n is 1.
3. A compound as recited in claim 2 wherein A is O.
4. A compound as recited in claim 3 wherein $X^1$ and $X^2$ are each chlorine.
5. A compound as recited in claim 4 wherein
$R^1$ is hydrogen or $C_1$–$C_6$ alkyl;
$R^2$ is $C_1$–$C_6$ alkyl, $C_1$–$C_4$ alkylidene, or $CH_2OR^5$;
$R^3$ is hydrogen, chlorine, bromine, or $OR^6$;
$R^4$ is $C_4$–$C_6$ alkyl, $C_2$–$C_6$ alkenyl, or $C_6$–$C_{12}$ aryl;
$R^5$ is hydrogen, $C_1$–$C_6$ alkyl, $C_2$–$C_6$ alkenyl, phenyl or naphthyl; and
$R^6$ is hydrogen or $C_1$–$C_6$ alkyl, wherein $R^3$ is absent when $R^2$ is $C_1$–$C_4$ alkylidene.

6. A compound as recited in claim 5 wherein
$R^1$ is hydrogen or $C_1$–$C_4$ alkyl;
$R^2$ is $C_1$–$C_4$ alkyl, $C_1$–$C_2$ alkylidene, or $CH_2OH$;

$R^3$ is hydrogen or chlorine; and
$R^4$ is $C_4$ alkyl, $C_2$–$C_4$ alkenyl, phenyl or naphthyl, wherein $R^3$ is absent when $R^2$ is $C_1$–$C_2$ alkylidene.

7. A compound as recited in claim 6 wherein
$R^1$ is hydrogen or methyl;
$R^2$ is methyl, methylene, or $CH_2OH$;
$R^3$ is hydrogen or chlorine;
$R^4$ is $C_4$ alkyl, wherein $R^3$ is absent when $R^2$ is methylene.

8. A compound as recited in claim 7 having the formula

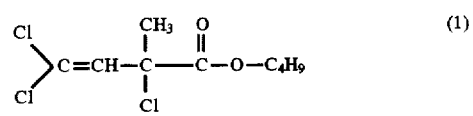

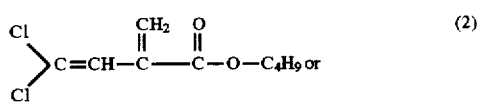

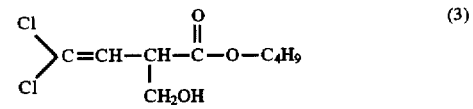

9. A composition useful in the production of ethylene copolymers comprising two or more compounds as recited in claim 1.

10. A composition as recited in claim 9 comprising two or more compounds as recited in claim 8.

11. A composition useful in the production of ethylene copolymers comprising:

a) 10 to 95 weight percent of one or more compounds of the formula:

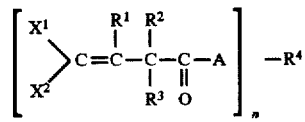

wherein n is 1;
$X^1$ and $X^2$ are each, independently, chlorine or bromine,
A is O or S;
$R^1$ is hydrogen or $C_1$–$C_{16}$ alkyl;
$R^2$ is $C_1$–$C_{16}$ alkyl, $C_6$–$C_{16}$ aryl, $C_1$–$C_4$ alkylidene, or $CH_2OR^5$;
$R^3$ is hydrogen, chlorine, bromine, or $OR^6$;
$R^4$ is $C_1$–$C_{16}$ alkyl, $C_7$–$C_{16}$ aralkyl, $C_2$–$C_{16}$ alkenyl, or $C_6$–$C_{18}$ aryl;
$R^5$ is hydrogen, $C_1$–$C_{16}$ alkyl, $C_7$–$C_{16}$ aralkyl, $C_2$–$C_{16}$ alkenyl, or $C_6$–$C_{18}$ aryl; and
$R^6$ is hydrogen or $C_1$–$C_{16}$ alkyl, wherein $R^3$ is absent when $R^2$ is $C_1$–$C_4$ alkylidene; and b) about 5 to 90 weight percent of one or more compounds selected from the compounds of the formula:

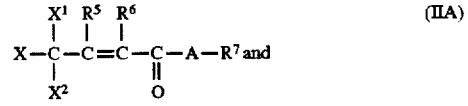

-continued $$X-\underset{\underset{X^2}{|}}{\overset{\overset{X^1}{|}}{C}}-\underset{\underset{H}{|}}{\overset{\overset{R^5}{|}}{C}}-\underset{\underset{X^3}{|}}{\overset{\overset{R^8}{|}}{C}}-\overset{\overset{}{}}{\underset{\underset{O}{\|}}{C}}-A-R^7 \quad (IIB)$$

wherein:

X, $X^1$, $X^2$ and $X^3$ are each, independently, chlorine or bromine;

A is oxygen or sulfur;

$R^5$ is hydrogen or $C_1-C_{16}$ alkyl, preferably, hydrogen or $C_1-C_6$ alkyl;

$R^6$ is $C_1-C_{16}$ alkyl, preferably, $C_1-C_6$ alkyl;

$R^7$ is hydrogen, $C_1-C_{16}$ alkyl, $C_2-C_{16}$ alkenyl, or $C_6-C_{18}$ aryl, preferably, hydrogen or $C_2-C_{12}$ alkyl; and $R^8$ is hydrogen, $C_1-C_{16}$ alkyl or $C_1-C_4$ alkylidene, preferably, hydrogen or $C_1-C_6$ alkyl, wherein $X^3$ is absent when $R^8$ is $C_1-C_4$ alkylidene.

12. A composition as recited in claim 11 wherein $R^5$ is hydrogen or $C_1-C_6$ alkyl;

$R^6$ is $C_1-C_6$ alkyl;

$R^7$ is hydrogen or $C_2-C_{12}$ alkyl; and $R^8$ is hydrogen or $C_1-C_6$ alkyl.

13. A composition useful in the production of ethylene copolymers comprising about 30 to 90 weight percent of one or more compounds as recited in claim 8 and about 10 to 70 weight percent of one or more compounds selected from the group consisting of compounds of the formula $$Cl-\underset{\underset{Cl}{|}}{\overset{\overset{Cl}{|}}{C}}-\underset{\underset{H}{|}}{\overset{\overset{H}{|}}{C}}-\underset{\underset{Cl}{|}}{\overset{\overset{CH_3}{|}}{C}}-\overset{\overset{}{}}{\underset{\underset{O}{\|}}{C}}-O-C_4H_9 \text{ and}$$

$$\underset{H}{\overset{Cl_3C}{>}}C=C\underset{C(O)-OC_4H_9}{\overset{CH_3}{<}}$$

14. A process for the preparation of alpha-olefin polymers comprising reacting ethylene, at least one monomer having the structural formula $CH_2$=CHQ where Q is an alkyl having 1 to 8 carbon atoms and, optionally, a non-conjugated diene, in the presence of a catalytically effective amount of a catalyst composition comprising:

(a) a vanadium-containing compound;

(b) an organoaluminum compound; and (c) one or more compounds of the formula:

$$\left[\underset{X^2}{\overset{X^1}{>}}C=C-\underset{\underset{R^3}{|}}{\overset{\overset{R^1}{|}}{C}}-\overset{\overset{R^2}{|}}{\underset{\underset{O}{\|}}{C}}-A\right]_n -R^4$$

wherein n is 1, 2, 3, or 4;

$X^1$ and $X^2$ are each, independently, chlorine or bromine;

A is O or S;

$R^1$ is hydrogen or $C_1-C_{16}$ alkyl;

$R^2$ is $C_1-C_{16}$ alkyl, $C_6-C_{16}$ aryl, $C_1-C_4$ alkylidene, or $CH_2OR^5$;

$R^3$ is hydrogen, chlorine, bromine, or $OR^6$;

$R^4$ is $C_1-C_{16}$ alkyl, $C_7-C_{16}$ aralkyl, $C_2-C_{16}$ alkenyl, or $C_6-C_{18}$ aryl;

$R^5$ is hydrogen, $C_1-C_{16}$ alkyl, $C_7-C_{16}$ aralkyl, $C_2-C_{16}$ alkenyl, or $C_6-C_{18}$ aryl; and $R^6$ is hydrogen or $C_1-C_{16}$ alkyl, wherein $R^3$ is absent when $R^2$ is $C_1-C_4$ alkylidene.

15. A process as recited in claim 14 wherein n is 1.

16. A process for the preparation of alpha-olefin polymers comprising reacting ethylene, at least one monomer having the structural formula $CH_2$=CHQ where Q is an alkyl having 1 to 8 carbon atoms and, optionally, a non-conjugated diene, in the presence of a catalytically effective amount of a catalyst composition comprising:

(a) a vanadium-containing compound;

(b) an organoaluminum compound; and (c) one or more compounds as recited in claim 8.

17. A process for the preparation of alpha-olefin polymers comprising reacting ethylene, at least one monomer having the structural formula $CH_2$=CHQ where Q is an alkyl having 1 to 8 carbon atoms and, optionally, a non-conjugated diene, in the presence of a catalytically effective amount of a catalyst composition comprising:

(a) a vanadium-containing compound;

(b) an organoaluminum compound; and (c) a composition as recited in claim 11.

18. A process for the preparation of alpha-olefin polymers comprising reacting ethylene, at least one monomer having the structural formula $CH_2$=CHQ where Q is an alkyl having 1 to 8 carbon atoms and, optionally, a non-conjugated diene, in the presence of a catalytically effective amount of a catalyst composition comprising:

(a) a vanadium-containing compound;

(b) an organoaluminum compound; and (c) a composition as recited in claim 13.

19. A process for the preparation of EPDM comprising reacting ethylene, propylene, and a non-conjugated diene, in the presence of a catalytically effective amount of a catalyst composition comprising:

(a) a vanadium-containing compound;

(b) an organoaluminum compound; and (c) one of more compounds of the formula:

$$\left[\underset{X^2}{\overset{X^1}{>}}C=C-\underset{\underset{R^3}{|}}{\overset{\overset{R^1}{|}}{C}}-\overset{\overset{R^2}{|}}{\underset{\underset{O}{\|}}{C}}-A\right]_n -R^4$$

wherein n is 1, 2, 3, or 4;

$X^1$ and $X^2$ are each, independently, chlorine or bromine;

A is O or S;

$R^1$ is hydrogen or $C_1-C_{16}$ alkyl;

$R^2$ is $C_1-C_{16}$ alkyl, $C_6-C_{16}$ aryl, $C_1-C_4$ alkylidene, or $CH_2OR^5$;

$R^3$ is hydrogen, chlorine, bromine, or $OR^6$;

$R^4$ is $C_1-C_{16}$ alkyl, $C_7-C_{16}$ aralkyl, $C_2-C_{16}$ alkenyl, or $C_6-C_{18}$ aryl;

$R^5$ is hydrogen, $C_1-C_{16}$ alkyl, $C_7-C_{16}$ aralkyl, $C_2-C_{16}$ alkenyl, or $C_6-C_{18}$ aryl; and $R^6$ is hydrogen or $C_1-C_{16}$ alkyl, wherein $R^3$ is absent when $R^2$ is $C_1-C_4$ alkylidene.

20. EPDM produced in accordance with the process as recited in claim 19.

21. A process for the preparation of EPM comprising reacting ethylene and propylene, in the presence of a catalytically effective amount of a catalyst composition comprising:

(a) a vanadium-containing compound;
(b) an organoaluminum compound; and
(c) one or more compounds of the formula:

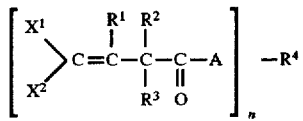

wherein
n is 1, 2, 3, or 4;
$X^1$ and $X^2$ are each, independently, chlorine or bromine;
A is O or S;
$R^1$ is hydrogen or $C_1$–$C_{16}$ alkyl;
$R^2$ is $C_1$–$C_{16}$ alkyl, $C_6$–$C_{16}$ aryl, $C_1$–$C_4$ alkylidene, or $CH_2OR^5$;
$R^3$ is hydrogen, chlorine, bromine, or $OR^6$;
$R^4$ is $C_1$–$C_{16}$ alkyl, $C_7$–$C_{16}$ aralkyl, $C_2$–$C_{16}$ alkenyl, or $C_6$–$C_{18}$ aryl;
$R^5$ is hydrogen, $C_1$–$C_{16}$ alkyl, $C_7$–$C_{16}$ aralkyl, $C_2$–$C_{16}$ alkenyl, or $C_6$–$C_{18}$ aryl; and
$R^6$ is hydrogen or $C_1$–$C_{16}$ alkyl, wherein $R^3$ is absent when $R^2$ is $C_1$–$C_4$ alkylidene.

22. EPM produced in accordance with the process as recited in claim 21.

23. In a process for the production of a copolymer of ethylene with at least one comonomer selected from the group consisting of copolymerizable mono-alphaolefins and nonconjugated polyenes, which process comprises reacting the ethylene with the comonomer in the presence of a catalyst composition comprising a vanadium-containing compound, an organoaluminum compound, and a catalyst promoter, wherein the improvement comprises a promoter comprising one or more compounds of the formula:

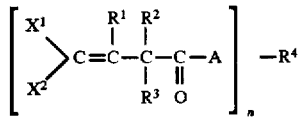

wherein
n is 1, 2, 3, or 4;
$X^1$ and $X^2$ are each, independently, chlorine or bromine;
A is O or S;
$R^1$ is hydrogen or $C_1$–$C_{16}$ alkyl;
$R^2$ is $C_1$–$C_{16}$ alkyl, $C_6$–$C_{16}$ aryl, $C_1$–$C_4$ alkylidene, or $CH_2OR^5$;
$R^3$ is hydrogen, chlorine, bromine, or $OR^6$;
$R^4$ is $C_1$–$C_{16}$ alkyl, $C_7$–$C_{16}$ aralkyl, $C_2$–$C_{16}$ alkenyl, or $C_6$–$C_{18}$ aryl;
$R^5$ is hydrogen, $C_1$–$C_{16}$ alkyl, $C_7$–$C_{16}$ aralkyl, $C_2$–$C_{16}$ alkenyl, or $C_6$–$C_{18}$ aryl; and
$R^6$ is hydrogen or $C_1$–$C_{16}$ alkyl, wherein $R^3$ is absent when $R^2$ is $C_1$–$C_4$ alkylidene.

* * * * *